United States Patent [19]

Robertson et al.

[11] Patent Number: 5,024,995
[45] Date of Patent: Jun. 18, 1991

[54] NATURAL PULMONARY SURFACTANT, METHOD OF PREPARATION AND PHARAMCEUTICAL COMPOSITIONS

[75] Inventors: Bengt Robertson; Tore Curstedt, both of Stockholm, Sweden

[73] Assignee: Chiesi Farmaceutici S.P.A., Perma, Italy

[21] Appl. No.: 177,771

[22] Filed: Apr. 5, 1988

[30] Foreign Application Priority Data

Apr. 8, 1987 [IT] Italy .................. 20032 A/87

[51] Int. Cl.$^5$ .................. A61K 37/22; A61K 31/685
[52] U.S. Cl. ........................ 514/21; 424/557; 514/2; 514/78; 514/975; 520/350; 520/359
[58] Field of Search .................. 514/2, 21, 78, 975; 530/350, 359, 417; 424/95, 557

[56] References Cited

U.S. PATENT DOCUMENTS 4,312,860  1/1982  Clements ........................ 514/78
4,338,301  7/1982  Tetsuro et al. ................... 424/95
4,397,839  8/1983  Tanaka .......................... 424/95
4,603,124  7/1986  Takei et al. .................... 514/2 X
4,765,987  8/1988  Bonte et al. .................... 514/78 X

FOREIGN PATENT DOCUMENTS 8706943  11/1987  PCT Int'l Appl. ................ 514/2

Primary Examiner—Howard E. Schain
Attorney, Agent, or Firm—Bucknam and Archer

[57] ABSTRACT

A pulmonary surfactant of animal origin made up of a high percentage of phospholipids ($\simeq 99\%$), by a protein fraction and characterized by the absence of carbohydrates and cholesterol.

The surfactant of the invention, obtained through filtration, centrifugation and extraction and by chromatography in inverse phase, allows better therapeutic results in the treatment of infant and adult respiratory distress syndromes (IRDS and ARDS).

4 Claims, No Drawings

NATURAL PULMONARY SURFACTANT, METHOD OF PREPARATION AND PHARAMCEUTICAL COMPOSITIONS

Subject of the invention is a pulmonary surfactant (PS) preparation of animal origin, with a low toxicity and optimal surface characteristics, for use in the prevention and therapy of IRDS (Infant Respiratory Distress Syndrome) and ARDS (Adult Respiratory Distress Syndrome) related to HMD (Hyaline Membrane Disease).

Normal pulmonary functionality depends on the presence of a particular material, the pulmonary surfactant, which is in charge of stabilizing the alveoli by reducing surface tension, in particular during the expiration phase.

The presence of pulmonary surfactant is of particular importance at the moment of birth.

Lack of PS is a key factor in the pathogenesis of IRDS, a disease which affects 10-15% of premature newborn babies. These subjects require artificial ventilation with high oxygen concentration and high insufflation pressure. IRDS death rate is around 25% and several of the survivors are left with chronic pulmonary complications mainly due to the prolonged artificial ventilation, and with secondary neurologic disfunctions due to cerebral hypoxia damage.

Lack of pulmonary surfactant is an important factor also in ARDS. This pathology can develop in cases of multiple trauma, aspiration, pancreatitis, etc. with a 40-70% death rate.

Administration of supporting doses of the lacking surfactant has proved useful in the treatment of these pathologies.

The pulmonary surfactants known to the art belong to three fundamental groups:

1. ARTIFICIAL PULMONARY SURFACTANT

Preparations of artificial surfactants with a base of dipalmitoyldyphosphocholine or of phospholipid mixtures in variable concentrations and ratios, optionally coupled with components such as sugars, aminoacids, alcohols or fat acids have been described in several patents: DE 2900300 (Klitzing LV); JP 58222022 (Teijin KK); EP 110498; U.S. Pat. No. 4312860 (University of California); DE 3229179 (Natterman A & Cie GmbH); JP 61065821 (Tokyo Tanabe KK).

At clinical-pharmacological level, however, the artificial surfactant did not prove to be very effective.

2. HUMAN PULMONARY SURFACTANT

Derived by extraction from amniotic liquid.

Although effective, it has proved to be of little practical utility, both for its high protein contents (which can lead to sensitization of the treated subject) and for difficulties of preparation on a large scale, as to obtain a dose an amniotic-liquid-taking from three terminal pregnancies is necessary. It also presents a high risk of viral contamination with possible transmission of pathologies as serious as AIDS.

3. NATURAL PULMONARY SURFACTANT

Extracted from mammal lung and with an effectivenes comparable to the human surfactant, it presents the great advantage of simplicity in preparation and a lower protein contents.

Pulmonary surfactants of natural origin of animal extraction have been prepared before. For instance, DE 3021006, JP 58045299 and EP 119056 (Tokyo Tanabe KK), describe a rather complex method which, through a series of operations such as repeated centrifugations ($850 \times g$ to $20,000 \times g$), lyophilization and various extractions, leads to a natural PS containing, besides phospholipids (75-95.5%) and proteins (0.5-5%), also carbohydrates (0.1-2%), neutral lipids (0.3-14%) and total cholesterol (0-8%), components of no use to the pharmacological action.

Also the surfactant prepared according to EP 145005 (Veb Arzneimittel Dresden) contains, in an even higher percentage (5-40%), an apolar lipid fraction, of no use to the biological activity and has instead low contents (40-70%) of phospholipids which represent on the contrary the most important physiological component.

Finally EP 55041, JP 58183620, JP 58183621, JP 58164513 (Tejin KK) describe natural, artificial or seminatural (i.e. added with synthetic phospholipids) surfactants totally de-proteinized. And the most recent studies have yet attributed to the presence of proteins a considerable functional meaning.

After long and profound studies, started several years ago, applicant has prepared a new pulmonary surfactant, subject of the present invention, whose composition is optimum for a balanced pharmacological activity.

A preparation process of this surfactant has also been worked out which, through the use of animal lung, allows to attain with few operations separation of the required fraction.

A first aspect of the invention refers therefore to an animal pulmonary surfactant presenting the following characteristics:

(a) the highest polar lipids concentration (99%), mainly phospholipids, as regards to other preparations;

(b) total absence both of free carbohydrates, cholesterol, triglycerides and cholesterol esters, components of no use for surface activity (Suzuki Y., J. Lipid Res. 23, 62-69, 1982) and of other neutral lipids ineffective from the pharmacological point of view (Nohara K., Eur. J. Resp. Dis. 69, 321-335, 1986);

(c) the presence of a protein component, characterized by a particularly high presence of hydrophobic amino acids, whose maximum concentration is lower than 1-1.5%. The proteic part is made up exclusively of hydropholic proteins of molecural weight ranging from 3 to 4 K (K=kilodaltons), which are important for absorption of the phospholipids at the air-liquid interface level.

A second aspect of the invention refers to a preparation method which through a simple process, reproduceable and feasible on industrial scale, allows to obtain a surfactant of the indicated characteristic.

Triturated animal lungs are washed in a physiological solution. They are filtered and centrifuged at speeds between 1,000 and $5,000 \times g$ for a time of one to three hours, according to the speed.

Extraction of the surfactant is then carried out with an organic solvent, preferably made up of a 1:2 methyl alcohol/chloroform mixture. The organic phase is water-washed and evaporated, thus obtaining a raw lipid fraction which is recovered with organic solvent, preferably formed by a 1,2-dichloroethane/dichloromethane mixture in a 1:4 ratio. Subsequently, by gel chromatography, the polar lipid component, made of phospholipids, is separated from the apolar one, made up of triglycerides, cholesterol and cholesterol esters.

The phospholipid fraction, the one for clinical use, is sterilized by ultrafiltration and stored at a temperature of at least −20° C. In the alternative, it can be lyophilized and stored at −20° C.

The preparation of the surfactant subject of the present invention is exemplified in detail hereinafter, without limiting it in any way.

EXAMPLE 1

Pig lungs are triturated in a mixer and the tissue fragments are washed in a physiological solution. The mixture is filtered and subjected to preliminary centrifugation at $1,000 \times g$ at 20° C. for 15 min., to eliminate cellular fragments. The supernatant liquor is then re-centrifuged at $3,00 \times g$ at 4° C. for 2 hours.

The raw (solid) surfactant is removed and extracted with 2:1 chloroform/methyl alcohol (V/V), filtered, washed with water and the organic phase is evaporated thus obtaining a raw lipid extract. The lipid fraction extract (1-1.5 g) is recovered with 20 ml of 1:4 1,2-dichloroethane/methyl alcohol mixture (V/V) and separated by chromatography in reverse phase on LIPI-DEX -5000 (4×21.5 cm; Packard Instruments Co.) column with a 1,2-dichloroethane/methyl alcohol 1:4 (V/V) eluant and a flow of 60-90 ml/h. Fraction 1 (0-270 ml) contains only phospholipids, fraction 2 (270-405 ml) contains few phospholipids and other polar lipids, while the apolar lipids (triglycerides, cholesterol and its esters) are kept by the column.

Fraction 1 can be used as such.

It is possible to recover the phospholipids contained in fraction 2 by proceeding a follows. Fraction 2 is re-chromatographied on the same column and the first fraction which is obtained (0-270 ml) is joined to the fraction 1 of the previous chromatography. The two joined fractions are dried (at temperatures lower than 40° C.), dissolved in 98:2 chloroform/methyl alcohol (V/V), sterilized by filtration (prefilter 0.45 μm and filter 0.2 μm, and stored in a freezer at −20° C.

EXAMPLE 2

The phospholipid fraction obtained with the method described in example 1 is defrosted, always under sterilization, dried and re-suspended in a physiological solution by means of ultrasounds at a suitable frequency, i.e. 45-50 kilohertz, with energy at 50 Watts. This is a rather critical step in the process of obtaining an active product, as it has been experimentally verified in certain cases that even mild variations of the sonic frequency, while leaving unaltered the product's chemical and chemico-physical characteristics, may considerably influence the biological activity.

The suspension thus obtained is distributed in vials for subsequent therapeutic use in a concentration of 80 mg of phospholipids/ml of salt solution.

With the method described in Examples 1 and 2 it is possible to isolate from the lungs of an adult pig about 200 mg of pulmonar surfactant, approximately the contents of a dose of product for the treatment of IRDS. Higher doses are required for treatment of ARDS.

For each batch of product, evaluation of the phospholipids concentration and composition, and of the quantity of the other components was carried out each time. Protein contents were evaluated through analysis of the amino acids.

Table I illustrates the composition of a phospholipid fraction of a preparation obtained according to the method described in Example 1.

| Phospholipids | mol % |
|---|---|
| Phosphatidylcholine | 75.1 ± 3.3 |
| Phosphatidylethanolamine | 7.5 ± 2.7 |
| Phosphatidylserine | 1.2 ± 1.1 |
| Phosphatidylinositol | 7.2 ± 1.7 |
| Phosphatidylglycerol | 3.5 ± 1.3 |
| Lysophosphatidylcholine | 0.7 ± 0.5 |
| Sphingomyelin | 4.7 ± 1.7 |

In the description which follows, in the aim to simplify, reference is made to the phospholipid fraction only as the essential and predominant component of the therapeutic product.

The surface properties of each batch have also been evaluated at 37° C. with the pulsating bubble technique (Surfactometer International, Toronto, Canada) (Enhorning G., J. Appl. Physiol. 43, 198-203, 1977).

At a concentration of 10 mg/ml the preparation presents a minimum of surface tension <5 mN/m at 50% of surface compression in 5 min pulsation.

The sterility of the preparation was confirmed by the bacteriological analysis.

The effectiveness of this preparation was tested on animals, in cases both of spontaneous IRDS in premature newborn rabbits and of ARDS induced in guinea pigs through repeated pulmonary wash.

Tests on animals

For these tests (carried out according to the method described by Lachmann B. et al. Pediatr. Res., 15, 833-838, 1981) rabbits, prematurely born by Caesarian section on the 27th day of pregnancy, immediately tracheotomized and incannulated, were used.

Eleven of these rabbits were treated by administering, through the cannula, pulmonar surfactant prepared as described in the present invention, while 15 others did not receive anything and made up the control group.

All the animals, the treated and the control ones, were parallely connected with an artificial respirator, kept under artificial ventilation at constant pressure, with 100% oxygen, at 40 actions/min and subjected to a standardized sequence of insufflation pressure. The lungs were in fact first expanded by ventilating for 1 min at a pressure of 35 cm of $H_2O$. Pressure was then gradually lowered at different times down to 15 cm of $H_2O$. Finally it was again increased for 5 min up to 25 cm of $H_2O$. Tidal volume was measured every 5 min.

The results are shown in Table II.

| Time (min) | $P_I$ (cm $H_2O$) | TV (treated) (ml/kg) | TV (control) (ml/kg) |
|---|---|---|---|
| 5 | 25 | 34.5 | 2.2 |
| 10 | 25 | 34.0 | 2.0 |
| 15 | 25 | 34.5 | 2.2 |
| 20 | 20 | 25.0 | 1.3 |
| 25 | 15 | 8.1 | 1.0 |
| 30 | 25 | 40.0 | 3.0 |

A remarkable increase of the tidal volume was observed in the treated animals in comparison to the control ones.

Histologic analysis of paraffin lung sections, stained with hematoxylin and eosin examined microscopically, showed a remarkable increase of the volume of the alveolar compartment in the treated group.

Similar results were obtained by administering the surfactant, subject of the present invention, to guinea pigs with a respiratory insufficiency induced according to the method described by Berggren P. et al., Acta Anesthesiol. Scand. 30, 321-328, 1986.

In the treated cases, as shown in Table III, there is a quicker return to normal values of gas exchange in comparison to the control cases.

| Time (min) | Treated $paO_2$ (Kpa) | $PaCO_2$ (Kpa) | Control (Kpa) | |
|---|---|---|---|---|
| 0 * | 7.5 | 8.2 | 8.0 | 6.8 |
| 15 | 47 | 5.9 | 9.0 | 7.0 |
| 30 | 48 | 5.5 | 10.0 | 7.2 |
| 45 * | 50 | 5.3 | 10.1 | 7.0 |
| 60 | 55 | 5.0 | 10.3 | 6.9 |

* Time of instillation of a dose of PS in the treated animals.

Clinical Tests

Clinical surveys were carried out in specialized centres for premature newborn babies with Hyaline Membrane Disease, who revealed great respiratory insufficiency and, in spite of intermittent mechanical ventilation at positive pressure with oxygen percentage higher than 60%, presented hypoxia, hypercapnia and acidosis.

The results obtained in a controlled study, carried out on a group of 10 newborn babies, 5 treated with the invention's surfactant and 5 controls treated with conventional therapy, are reported hereinafter.

At the moment of treatment the patients were disconnected from the respirator and the surfactant was injected into the endotracheal tube at a dose of 2.5 ml/kg, equal to 200 mg of phospholipids/kg.

After administration the babies were ventilated manually with bubble for 1 min at a frequency of 40-60 actions/min and with the same gas mixture used previously.

The patients were then reconnected to the respirator set as previously; subsequent variations were made in accordance with clinical response and modification in the blood gases.

The babies making up the control group were also disconnected from the ventilator and ventilated manually for 2 min at the same conditions used for the patients treated with the surfactant.

The effectiveness of the treatment was documented by the movement of the various indexes on respiratory functionality.

In particular within about 5 min, $paO_2$ (Partial Arterial Oxygen Pressure) values were undergoing a rapid and dramatic increase so that the $pa/AO_2$ ratio (ratio between partial oxygen pressures at arterial level and at alveolar level) reached at 15 min a median value three time higher than the initial one (30.6 against 10.4; $p<0.001$), stabilizing then, after a slight decrease between the first and second hour, on values approx. double in comparison to the starting ones.

In the control group instead, the $pa/AO_2$ ratio did not show any notable change in the initial median value of 7.62.

Also the pulmonary radiologic findings documented improvement of the pathology in the treated subjects with a decrease in parenchimal fluid retention and in distension of bronchioli.

The radiologic findings on the babies of the control group instead did not reveal any significant change in the first 48-72 hours of observation.

It is important to point out finally that in the cases treated with the invention's pulmonary surfactant a significant reduction in the time of treatment with artificial ventilation at positive pressure and in the duration of the oxygen therapy was observed.

This allowed a reduction both in the duration of the intensive therapy, highly expensive, and of the risks connected to invasive treatments. Several authors in fact reckon that the pulmonary damage consequent to IRDS is linked also to the resuscitation therapy and in particular to the prolonged exposure to high oxygen concentrations.

Moreover, there was no evidence of immunological complications in the surviving patients, which confirms the low antigenicity of the surfactant of the invention.

The use of exogenous surfactant acquires therefore a considerable importance both in prevention and therapy of respiratory disease syndromes.

For the foreseen therapeutic use, phospholipid suspensions in physiologic solution of 80 mg/ml concentration, instilled in doses of 2.5 mlg/kg equal to about 200 mg of phospholipids/kg of body weight, have proved to be particularly suitable.

The treatment is normally carried out by direct endotracheal instillation of the suspension. Another possibility is administration by nebulization.

We claim:

1. An animal pulmonary surfactant which consists of polar lipids and proteins wherein the polar lipids are mainly phospholipids and the proteins are hydrophobic low molecular weight proteins of 3-14 KD (Kilodaltons), the polar lipid content is 98.5-99%, the protein content is less than 1.5%, and the phospholipid fraction contains at least 70-75% by weight of phosphatidylcholine, 40-45% of which consists of diplamitoylphosphatidylcholine, said surfactant is free of carbohydrates, cholesterol, triglycerides and cholesterol esters.

2. A process of preparation of a pulmonary surfactant which consists of an animal pulmonary surfactant consisting of polar lipids and proteins wherein the polar lipids are mainly phospholipids and the proteins are hydrophobic low molecular weight proteins of 3-14 KD (Kilodaltons), the polar lipid content is 98.5%-99%, the protein content is less than 1.5%, the phospholipid fraction contains at least 70-74% by weight of phosphatidylcholine, 40-45% of which consists of dipalmitoylphosphatidylcholine, and is free of carbohydrates, cholesterol, triglycerides and cholesterol esters, which comprises the steps of:
   (a) triturating animal lungs to obtain triturated lungs;
   (b) washing said triturated lungs in a salt solution and filtering off the filtrates to obtain a solid fraction;
   (c) centrifuging the solid fraction;
   (d) extracting with an organic solvent;
   (e) evaporating the solvent and
   (f) recovering the polar components by gel chromatography.

3. The process according to claim 2, wherein step (f) is carried out by chromatography in inverse phase on LIPIDEX -5000® column, with a 1,2-dichloroethane/methanol 1:4 (V/V).

4. A pharmaceutical composition for the cure of Infant Respiratory Distress Syndrome in premature infants and Adult Respiratory Distress Syndrome, in a suspension in vials for inhalation or endotracheal administration containing as active principle a pulmonary surfactant according to claim 1, the surfactant being suspended in physiological solution of concentration between 50 and 100 mg of phospholipids/ml.

* * * * *